United States Patent [19]

Cocoman et al.

[11] Patent Number: 4,962,206

[45] Date of Patent: Oct. 9, 1990

[54] PROCESS FOR THE PREPARATION OF 4-BROMOPHTHALIC ANHYDRIDE

[75] Inventors: Mary K. Cocoman; Willis T. Schwartz, both of Grand Island, N.Y.

[73] Assignee: Occidental Chemical Corporation, Niagara Falls, N.Y.

[21] Appl. No.: 439,299

[22] Filed: Nov. 20, 1989

[51] Int. Cl.$^5$ ............................................ C07D 307/77
[52] U.S. Cl. .................................. 549/246; 549/247; 549/307
[58] Field of Search .................... 549/307, 246, 247

[56] References Cited

U.S. PATENT DOCUMENTS

| | | | |
|---|---|---|---|
| 2,558,862 | 7/1951 | Liston et al. | 549/246 |
| 4,559,405 | 12/1985 | Telschow | 549/240 |
| 4,560,773 | 12/1985 | Telschow | 549/240 |
| 4,709,056 | 11/1987 | Catter et al. | 549/246 |

Primary Examiner—Mukund J. Shah
Assistant Examiner—Deborah D. Carr
Attorney, Agent, or Firm—James F. Tao; John H. Engelmann

[57] ABSTRACT

A process for the production of 4-bromophthalic anhydride which comprises the reaction of 4-chlorotetrahydrophthalic anhydride with elemental bromine, in the presence of a catalytically effective amount of iron or an iron salt is disclosed.

10 Claims, No Drawings

PROCESS FOR THE PREPARATION OF 4-BROMOPHTHALIC ANHYDRIDE

BACKGROUND OF THE INVENTION

This invention relates to a process for the preparation of 4-bromophthalic anhydride by reacting 4-chloro tetrahydrophthalic anhydride with bromine in the presence of iron. 4-Bromophthalic anhydride is useful as an intermediate for the preparation of various commercial products including polymers, dyes and plasticizers. It is particularly useful in the preparation of dianhydride monomers such as oxydiphthalic dianhydride which may be polymerized with a suitable diamine to form a polyimide. 4-Bromophthalic anhydride has been prepared by the reaction of phthalic anhydride, in aqueous alkali, with bromine, and subsequent acidification and dehydration (E. T. Sabourin, et al., J. Org. Chem., Vol. 48, 5137 (1983)). Our process produces 4-bromophthalic anhydride in better yields than we have been able to achieve using the method reported by Sabourin, et al.

4-Chloro tetrahydrophthalic anhydride may be prepared by the condensation of 2-chloro-1,3-butadiene with maleic anhydride. This reaction produces mostly 4-chlorotetrahydrophthalic anhydride with the double bond in the 4 position. A small percentage of product has the double bond in the 3 position. The presence of two isomers has no apparent effect upon the reactions which are the subject of this invention.

The dehydrogenation of tetrahydrophthalic anhydrides to yield phthalic anhydrides has been observed. For example, Bergmann, J. Amer. Chem. Soc. 64, 176 (1942) discloses the aromatization of tetrahydrophthalic anhydride products of Diels-Alder reactions. The author discloses that dehydrogenation occurred when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed.

U.S. Pat. No. 4,560,772 to Telschow discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. No. 4,560,773 to Telschow discloses a similar reaction between the electron rich 4-methyltetrahydrophthalic anhydride and bromine in the presence of a catalytic amount of an acid acceptor such as dimethylformamide or pyridine in the liquid phase.

Skvarchenko et al., Obshchei Khimii, Vol. 30, No. 11. pp. 3535-3541 disclose the aromatization of chloro-substituted tetrahydrophthalic anhydride by heating with phosphorus pentoxide. In the aromatization process described, however, decarboxylation also occurs with the formation of the corresponding chloro-substituted benzene compound. The preparation of various other tetrahydrophthalic acids and anhydrides and various methods for dehydrogenation and aromatization thereof are reviewed by Skvarchenko in Russian Chemical Review, No. 1963, pp. 571-589.

A co-pending application, Ser. No. 07/405,606, discloses that 4-chlorotetrahydrophthalic anhydride reacts with elemental bromine to form 4-chlorophthalic anhydride. 4-Bromophthalic anhydride is sometimes found as a side product in low percentage, but is not economically recoverable.

Iron catalyzes the bromination of aromatic molecules (ORGANIC CHEMISTRY, Louis F. Fieser and Mary Fieser, 3rd Edition, D. C. Heath and Company, Boston 1956, pages 644-645 and FUNDAMENTALS OF ORGANIC CHEMISTRY, 2nd Edition, T. W. Graham Solomons, John Wiley & Sons, New York 1986, pages 445-446 and 455). For example, benzene reacts with bromine, in the presence of iron, to form bromobenzene. Chlorobenzene, under similar conditions, forms bromochlorobenzene. Halogens and carboxyl groups, when substituted on a benzene ring, tend to de-activate the ring to further substitution. (Solomons, p. 455). The presence of three de-activating groups on the ring would be expected to cause ring bromination to be slow. In fact, we have found that under the reaction conditions used for the aromatization of 4-chlorotetrahydrophthalic anhydride, 4-chlorophthalic anhydride does not react with bromine in the presence of iron.

SUMMARY OF THE INVENTION

It has now been found that surprisingly, a mixture of 4-chlorophthalic anhydride and 4-bromophthalic anhydride is produced by the reaction of 4-chlorotetrahydrophthalic anhydride with elemental bromine in the presence of iron.

DETAILED DESCRIPTION OF THE INVENTION

Surprisingly, 4-chlorotetrahydrophthalic anhydride reacts with bromine, in the presence of iron, to form a mixture of 4-chlorophthalic anhydride and the 4-bromophthalic anhydride. 4-Chlorophthalic anhydride does not react with bromine under these reaction conditions. Accordingly, the 4-bromophthalic anhydride produced in the reaction does not come from the conversion of 4-chlorophthalic anhydride.

The process of this invention is carried out in the liquid phase, in the presence of a solvent, at atmospheric pressure or under applied or autogenous pressure at temperatures ranging from about 100° to about 200° Celsius and preferably about 110° to about 150° Celsius. Solvents that may be employed are preferably substantially non-reactive with bromine as well as with the starting material and products of the reaction. In addition, the solvents should dissolve both the starting material and the products of the reaction. The boiling point of the solvent is not a factor in conducting the reaction since the reactions may be conducted under pressure to achieve the temperature necessary for the reaction. Typical of the solvents that may be employed are aromatic solvents such as nitrobenzene, monohalobenzenes, and dihalobenzenes and aliphatic solvents such as chloroform, carbon tetrachloride, or chlorinated lower alkanes, including monochloro and polychloro alkanes, or polychlorinated lower alkenes. The most preferred solvent is chlorobenzene.

The iron catalyst may be added to the reaction mixture in the form of an iron salt, such as ferric chloride, ferric bromide, or as elemental iron. Iron salts, other than halides also function in this reaction because the presence of elemental bromine and traces of HBr from the dehydrogenation reaction are able to convert any salt of iron into a catalytically active form. Typically, 1 mole % (based upon starting material) of iron or an iron compound is a catalytically effective amount. However, it has been found that amounts of iron or an iron salt on the order of 0.04 mole have some catalytic effect. The effect of the iron in this reaction is as a catalyst and iron need not be added to the reaction provided that traces of iron from some other source are present. If the reactants or solvent contain trace impurities of iron, the catalytic effect of the iron in forming 4-bromophthalic anhydride will be observed.

This reaction produces a mixture of 4-bromophthalic anhydride and 4-chlorophthalic anhydride. For many uses, the mixture of the two anhydrides may be used without further purification. Where pure 4-bromophthalic anhydride is desired, it is possible to separate the 4-bromophthalic anhydride from the 4-chlorophthalic anhydride by careful distillation.

During the reaction it is preferred to condense the exiting vapors at a temperature sufficient to condense bromine, but allow HBr to escape (to be recovered by scrubbers for other uses).

The following specific examples are provided to further illustrate this invention and the manner in which it may be carried out. It will be understood, however, that the specific details given in the examples have been chosen for purposes of illustration and are not to be construed as a limitation on the invention. In the examples, unless otherwise indicated, all parts and percentages are by weight and all temperatures are in degrees Celsius.

EXAMPLE 1

37.3 grams of 4-chlorotetrahydrophthalic anhydride were added to 5.6 grams of chlorobenzene. The mixture was heated to 150° C. 0.36 grams of ferric chloride were added. The temperature was maintained at 150° C. while 63.9 grams of bromine were added over a nine hour period. The reaction mixture was then heated for four more hours at 165° C. The mixture was analyzed by a gas chromatographic method in which the area corresponding to each product was compared to the total area. The results indicated that the reaction mixture contained 58.5% 4-chlorophthalic anhydride and 31.8% 4-bromophthalic anhydride.

EXAMPLE 2

37.3 grams of 4-chlorotetrahydrophthalic anhydride were dissolved in 5.6 grams of chlorobenzene and heated to 110° C. 0.11 grams of iron powder were added. The temperature of the reaction mixture was maintained at 110° C. while 44.8 grams of bromine were added dropwise over a five hour period. The reaction mixture was then warmed to 135° C. and 19.2 grams of bromine were added. The reaction mixture was heated to 165° C. for 3½ hours. The mixture was analyzed by a gas which involved comparison of the peak areas corresponding to various compounds to the total peak area. The results indicated that 29.3% of 4-chlorophthalic anhydride and 41.6% of 4-bromophthalic anhydride had been produced.

EXAMPLE 3

A mixture of 559.5g (3.0 moles) of 4-chlorotetrahydrophthalic anhydride and 84.0 g of monochlorobenzene was heated and maintained at 105° C. while 720.0 g (4.5 moles) of bromine were added over a three hour period at which time a sample of the reaction mixture was analyzed by gas chromatography and found to contain 47% (g.c. area %) 4-chlorophthalic anhydride. The reaction mixture was heated to 135° C. and maintained thereat for 3 hours while 240.0 g (1.5 moles) of bromine were added slowly, then heated to 165°–170° C. over a 20-minute period. A sample was analyzed and found to contain 79% 4-chlorophthalic anhydride. The temperature was maintained at about 165°–170° C. while 30g (0.1875 mole) bromine were added over a 35-minute period. Temperature was maintained for an additional 5 hours. Final analysis by gas chromatography indicated (in area %) 94.7% 4-chlorophthalic anhydride, 2.1% bromophthalic anhydride and no detectable 4-chlorotetrahydrophthalic anhydride starting material.

EXAMPLE 4

36.5 grams of 4-chlorophthalic anhydride were dissolved in 5.5 grams of chlorobenzene. The mixture was heated to 110° C. 0.029 grams of iron powder was added and 10 grams of bromine were added over a three hour period. The reaction temperature was increased to 135° C. and another 5 grams of bromine were added. The reaction mixture was then heated to 165° C. and another 6.2 grams of bromine were added. The mixture was analyzed by a gas chromatographic method and it was found that the 4-chlorophthalic anhydride had not reacted to form 4-bromophthalic anhydride.

EXAMPLE 5

18.65 grams of 4-chlorotetrahydrophthalic anhydride were dissolved in 2.8 grams chlorobenzene and heated to 110° C. 0.0026 grams iron powder were added. The temperature of the reaction mixture was maintained at 110° C. while 22.4 grams of bromine were added over a 2 hour period. The reaction temperature was then increased to 130° C. and an additional 9.6 grams of bromine were added over a 1½ hour period. The reaction temperature was then increased to 165°–170° C. for 4 hours and the resulting mixture contained 76.7% 4-chlorophthalic anhydride and 7.8% 4-bromophthalic anhydride (GC area %).

We claim:

1. A process for the production of a mixture of 4-chlorophthalic anhydride and 4-bromophthalic anhydride which comprises the reaction of 4-chlorotetrahydrophthalic anhydride, in a suitable solvent, with elemental bromine in the presence of a catalytically effective amount of a catalyst selected from the group consisting of elemental iron and iron salts.

2. A process according to claim 1 wherein said solvent is a monohalobenzene.

3. A process according to claim 1 wherein said solvent is nitrobenzene.

4. A process according to claim 1 wherein said solvent is a dihalobenzene.

5. A process according to claim 1 wherein said solvent is a chlorinated lower alkane.

6. A process according to claim 1 wherein said solvent is a polychlorinated lower alkene.

7. A process according to claim 1 wherein said catalyst is elemental iron.

8. A process according to claim 7 wherein said solvent is chlorobenzene.

9. A process according to claim 1 wherein said catalyst is an iron halide.

10. A process according to claim 9 wherein said solvent is chlorobenzene.

* * * * *